(12) United States Patent
Mijares et al.

(10) Patent No.: US 8,177,793 B2
(45) Date of Patent: May 15, 2012

(54) SURGICAL STAPLE REMOVER

(75) Inventors: Michael J. Mijares, Miami Lakes, FL (US); Mark Sinnreich, Miami Beach, FL (US); William Sinnreich, Boynton Beach, FL (US)

(73) Assignee: Sinn Rx, LLC, Miami Beach, FL (US)

( * ) Notice: Subject to any disclaimer, the term of this patent is extended or adjusted under 35 U.S.C. 154(b) by 0 days.

(21) Appl. No.: 13/045,509

(22) Filed: Mar. 10, 2011

(65) Prior Publication Data

US 2011/0224694 A1 Sep. 15, 2011

Related U.S. Application Data

(60) Provisional application No. 61/312,327, filed on Mar. 10, 2010.

(51) Int. Cl.
*A61B 17/10* (2006.01)

(52) U.S. Cl. ........................................................ 606/138

(58) Field of Classification Search .................... 606/138
See application file for complete search history.

(56) References Cited

U.S. PATENT DOCUMENTS

| | | | |
|---|---|---|---|
| 1,948,096 A * | 2/1934 | Cavanagh | ...................... 254/28 |
| 4,026,520 A | 5/1977 | Rothfuss et al. | |
| 4,073,179 A | 2/1978 | Hickey et al. | |
| D271,742 S | 12/1983 | Li et al. | |
| 4,487,394 A | 12/1984 | Rothfuss et al. | |
| 4,515,348 A * | 5/1985 | Blake | ............................ 254/28 |
| D280,019 S | 8/1985 | Meyer et al. | |
| D281,624 S | 12/1985 | Babini | |
| D283,048 S | 3/1986 | Sharkany | |
| D287,279 S | 12/1986 | Lazickas | |
| 4,685,460 A | 8/1987 | Thornton | |
| 4,805,876 A | 2/1989 | Blake et al. | |
| D302,466 S | 7/1989 | Porat et al. | |
| D308,807 S | 6/1990 | Yu | |
| 5,236,435 A | 8/1993 | Sewell, Jr. | |
| 5,364,406 A | 11/1994 | Sewell, Jr. | |
| 5,451,231 A | 9/1995 | Rabenau et al. | |
| 5,938,178 A | 8/1999 | Oh | |
| 5,957,430 A | 9/1999 | Olson | |
| 6,105,936 A | 8/2000 | Malek | |
| D438,965 S * | 3/2001 | Porat | .......................... D24/133 |
| 6,391,035 B1 | 5/2002 | Appleby et al. | |
| 6,513,788 B1 | 2/2003 | Ashe | |
| 6,641,114 B1 | 11/2003 | Davis | |
| 7,048,255 B2 | 5/2006 | Buch et al. | |
| 7,090,198 B1 | 8/2006 | Gurmu | |
| 7,131,977 B2 | 11/2006 | Fowler | |

* cited by examiner

*Primary Examiner* — Corrine M McDermott
*Assistant Examiner* — Son Dang
(74) *Attorney, Agent, or Firm* — Mark Terry (57) ABSTRACT

A surgical staple remover apparatus is disclosed. The surgical staple remover apparatus comprises a first elongated element having a handle on one end and a downward facing protrusion on the other end and a second elongated element having a handle on one end and an upwards sloped planar element on the other end, wherein the first and second elongated elements are pivotally connected. The apparatus further includes a cutout located at a midpoint of a tip of the upwards sloped planar element and a housing running a length of the second elongated element, beginning at the upwards sloped planar element and including an opening facing the planar element, such that surgical staples removed with the apparatus are drawn into the housing. The apparatus further includes a spring loaded element within the housing, wherein the spring loaded element grabs removed surgical staples and draws them into the housing.

20 Claims, 8 Drawing Sheets

SURGICAL STAPLE REMOVER

CROSS-REFERENCE TO RELATED APPLICATIONS

This patent application claims priority to provisional patent application No. 61/312,327, filed on Mar. 10, 2010 and entitled "Surgical Staple Remover." The subject matter of provisional patent application No. 61/312,327 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medical devices, and more particularly relates to the field of devices for automating the process of removing surgical staple's.

BACKGROUND OF THE INVENTION

The use of surgical staples in the medical industry for closing wounds or incisions in the skin of a patient has grown over the last decade due to its advantages over thread sutures. One of the main advantages of surgical staples over thread sutures is the reduced amount of time required for surgical staples to be implanted. In cases where large incisions are made, the use of surgical staples can, for example, reduce the length of time required for the suturing process and thus the length of time the patient must be maintained under anesthesia.

Conventional surgical staples comprise an elongated crown and an L-shaped portion on each end of the crown, wherein when implanted in a patient, the crown is located on the exterior of the skin of the patient and the L-shaped portions are bent in a downward direction so that the ends of the L-shaped portions are opposed, thereby incising and gripping the skin. The aforementioned conventional surgical staple may be removed from the skin of a patient by bending the staple crown into a U-shaped configuration. This causes the L-shaped legs of the staple to shift upwardly and outwardly so that they may be lifted away from the patient's skin.

Figure 1:
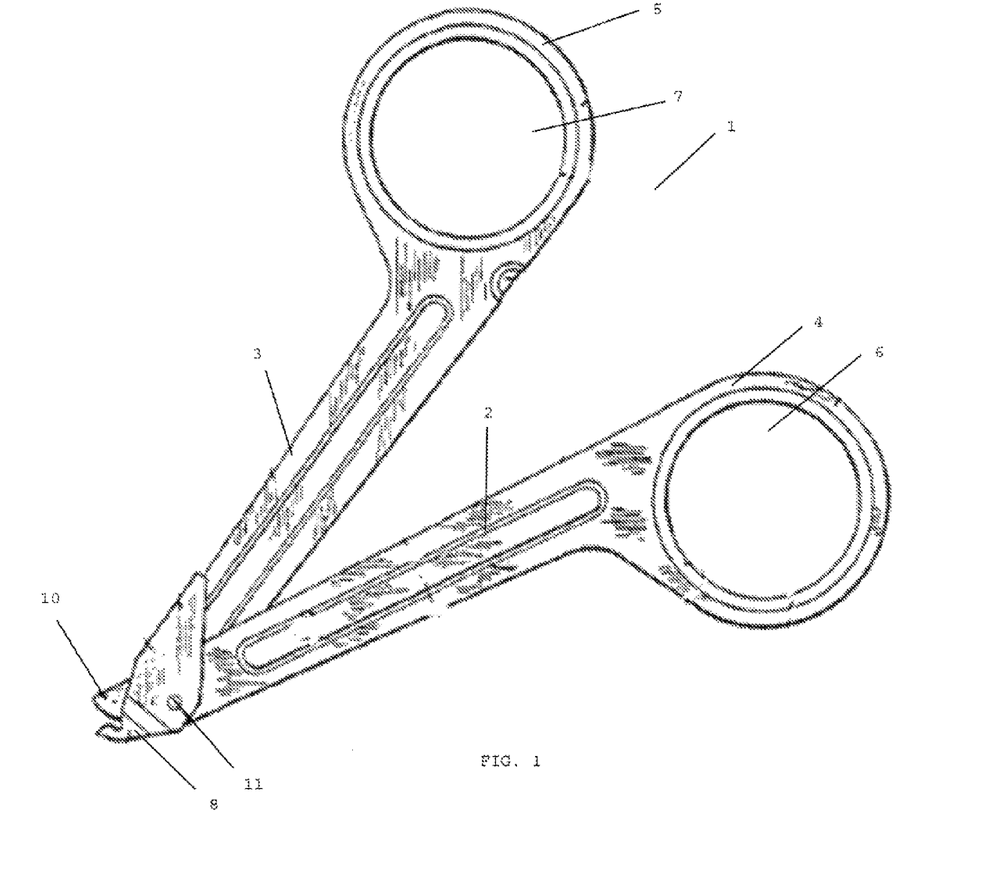
FIG. 1 is an illustration of a side view of a prior art surgical staple remover.

A conventional surgical staple remover 1, shown in FIG. 1, typically comprises a first handle 2 and a second handle 3 pivoted together at pivot point 11. Each handle includes circular finger inserts (4 and 5), each of which includes an orifice (6 and 7) for inserting a pair of fingers, such as a thumb and forefinger. The second handle 3 terminates in element 8 comprising two parallel, dual-pronged J-shaped units that are inserted under a surgical staple to be removed. The first handle 2 terminates in an anvil 10 that includes a downward facing footprint that is situated between the two units of the dual-pronged J-shaped element 8 and wherein the anvil 10 is placed on top of the crown of the surgical staple to be removed. When the conventional surgical staple remover 1 is gripped and contracted by a user, the downward facing footprint of anvil 10 applies force to the top of the crown of the surgical staple, thereby bending the staple crown into a U-shaped configuration. Consequently, the L-shaped legs of the staple are moved upwardly and outwardly, thereby lifting away from the patient's skin.

One of the disadvantages of a conventional surgical staple remover is that it does not adequately deal with the final disposition of the surgical staple being removed. It is common to have surgical staples jump into the air or fall away during removal. Personnel must then go about finding and disposing of the removed surgical staple and sterilizing anything the staple came into contact with. It is unsanitary to allow removed surgical staples to come into contact with individuals or things since implanted surgical staples have resided within a human's body and may contain biologically hazardous residue that could contaminate individuals and locations. Further, the process of cleaning up after the conventional removal of surgical staples is time consuming and expensive since proper decontamination and sterilization procedures, employing the use of costly protective equipment and cleaning materials, must be undertaken. Further, during an operation on a patient, it is imperative that all removed staples are accounted for, lest the removed staple falls into an open incision unnoticed.

Another disadvantage of a conventional surgical staple remover is that it requires that each removed surgical staple is immediately disposed of. That is, the doctor or technician must remove a surgical staple, place it in a receptacle, and then return to the wound to remove the next surgical staple. This is problematic as it requires that the doctor or technician temporarily lose sight of the wound while he disposes of the removed surgical staple.

Therefore, a need exists to overcome the problems the prior art as discussed above, and particularly for a more effective and efficient surgical staple remover, as well as a more sanitary and easy-to-operate surgical staple remover.

SUMMARY OF THE INVENTION

Briefly, according to an embodiment of the present invention, a surgical staple remover apparatus is disclosed. The surgical staple remover apparatus comprises:

(a) a first elongated element having a handle on one end and a downward facing protrusion on the other end;

(b) a second elongated element having a handle on one end and an upwards sloped planar element on the other end, wherein the first and second elongated elements are pivotally connected such that moving the handles into close proximity results in moving the protrusion and planar element into close proximity and such that moving the handles apart results in separating the protrusion and planar element;

(c) a cutout located at a midpoint of a tip of the upwards sloped planar element, such that moving the handles into close proximity results in moving the protrusion into the cutout of the planar element, wherein placing the planar element under a surgical staple and moving the handles into close proximity, results in the protrusion pressing against a crown of the surgical staple, thereby deforming the surgical staple so as to remove it;

(d) a housing running a length of the second elongated element, beginning substantially at the upwards sloped planar element and including an opening facing the planar element; and (e) a spring loaded element located within the housing and having a hook on a distal end, wherein when the handles are separated, the spring loaded element is laterally compressed and extends out of the housing so as to grip a removed surgical staple, and wherein when the handles are moved into close proximity, the spring loaded element is at rest and contracts into the housing with the removed surgical staple.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

FIG. 8 is a perspective view of the surgical staple remover showing its main components, in accordance with one embodiment of the present invention.

DETAILED DESCRIPTION

The present invention solves problems with the prior art by providing a simple and easy-to-use surgical staple remover that automatically captures removed surgical staples. The apparatus of the present invention improves upon the prior art by definitively dealing with the final disposition of each surgical staple being removed. The present invention eliminates the possibility of having surgical staples jump into the air or fall away during removal. The present invention further eliminates the necessity for personnel to find and dispose of the removed surgical staple and sterilize anything the staple came into contact with. This eradicates the potential for removed surgical staples to come into contact with, and contaminating, individuals or things. Further, the present invention eliminates the need to clean up after the conventional removal of surgical staples, thereby saving time and expense. Also, the present invention allows a doctor or technician to undergo the process of removing multiple surgical staples without losing sight of the wound during the process.

Finally, the present invention provides a surgical staple remover with a minimal number of component parts, thereby reducing the potential for failure or malfunction of the device. Also, the minimal number of component parts allows for quick and inexpensive fabrication of the surgical staple remover, thereby meeting the economic requirements for a disposable surgical staple remover.

Figure 2:
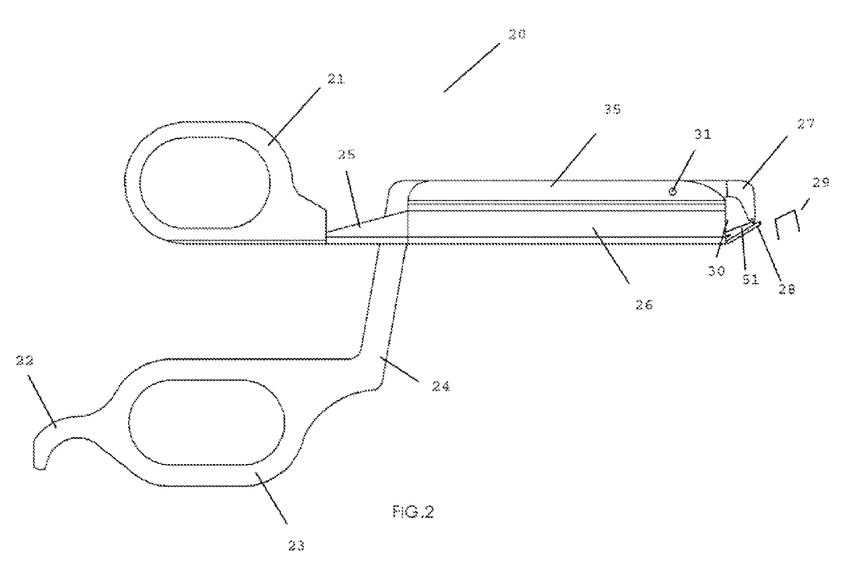
FIG. 2 is a side view of the surgical staple remover in an open position, in accordance with one embodiment of the present invention.

FIG. 2 is a side view of the surgical staple remover 20 in an open position, in accordance with one embodiment of the present invention. The apparatus 20 may be composed of a conventional medical device material such as stainless steel and other metal alloys; or a disposable material, such as plastic or a plastic derivative, so that the apparatus may be disposed after a single use, thereby eliminating the necessity for cleaning or sterilizing the apparatus between uses. First and second elongated elements 24, 25 may be stamp manufactured from a planar metallic sheet. See FIG. 8 which shows the main components of the surgical staple remover 20, comprising the first and second elongated elements 24, 25 and the interior element 50. The low number of parts, especially moving parts, and the simplicity of the design results in a surgical staple remover 20 that is straightforward and inexpensive to fabricate, thereby meeting the requirements for a disposable medical device.

The apparatus 20 may include a first elongated element 24 having a handle 23 on one end and a downward facing protrusion 27 on the other end. The element 24 may also include an additional finger rest 22 adjacent to the handle 23, which may comprise an oval shaped element for accommodating an individual's fingers. The downward facing protrusion 27 may comprise a curved element that protrudes downwards from one end of the first elongated element 24, the tip of which includes a footprint for placement on top of a crown of a surgical staple. Note that elongated element 24 may comprise two substantially right angles—one located distally from the handle 23 and the other located near the juncture of the elements 24 and 25.

The apparatus 20 may further include a second elongated element 25 having a handle 21 on one end and an upwards sloped planar element 28 on the other end, wherein the first and second elongated elements 24, 25 are pivotally connected at pivot point 31 such that moving the handles 21, 23 into close proximity results in moving the protrusion 27 and planar element 28 into close proximity and such that separating the handles results in separating the protrusion and planar element. The upwards sloped planar element 28 may comprise a triangular shaped element (see FIG. 3) having a size and shape that allow its complete insertion underneath a crown of a conventional surgical staple, such as staple 29. The upwards sloped planar element 28 may further comprise a cutout 34 located at a midpoint of a tip of the upwards sloped planar element 28, such that moving the handles 21, 23 into close proximity results in moving the protrusion 27 into the cutout of the planar element 28. Placement of the planar element 28 under a surgical staple and moving the handles 21, 23 into close proximity, results in the protrusion 27 pressing against the crown of the surgical staple, thereby deforming the surgical staple so as to remove it. The cutout may comprise the shape of a narrow strip that corresponds to, or accommodates, a profile of the protrusion 27.

The apparatus 20 may further include a housing 26 having an interior volume and running a length of the second elongated element 25, beginning at the upwards sloped planar element 28 and including an opening 30 facing the planar element 28, such that surgical staples removed with the apparatus are drawn into the housing 26. The housing 26 may comprise an elongated rectangular box running a length of the second elongated element 25. The housing 26 may also include a flange 35 that runs along a top length of the housing 26, and wherein the pivot point 31 is located in the flange. The flange 35 may comprise two parallel flanges that are in close proximity but having a gap between them, and wherein a portion of the second elongated element 24 is located within the gap when the handles 21, 23 are in close proximity (see FIG. 4). Note that elongated element 25 may not comprise any substantially right angles—comprising mainly one straight, elongated element that extends from the handle 21 to element 28.

FIG. 2 also shows the spring loaded element 51 extending, or protruding, from the opening 30 and onto the planar element 28, which is a result of the surgical staple remover 20 being in an open position. The action performed by the spring loaded element 51 is described in greater detail below.

Figure 3:
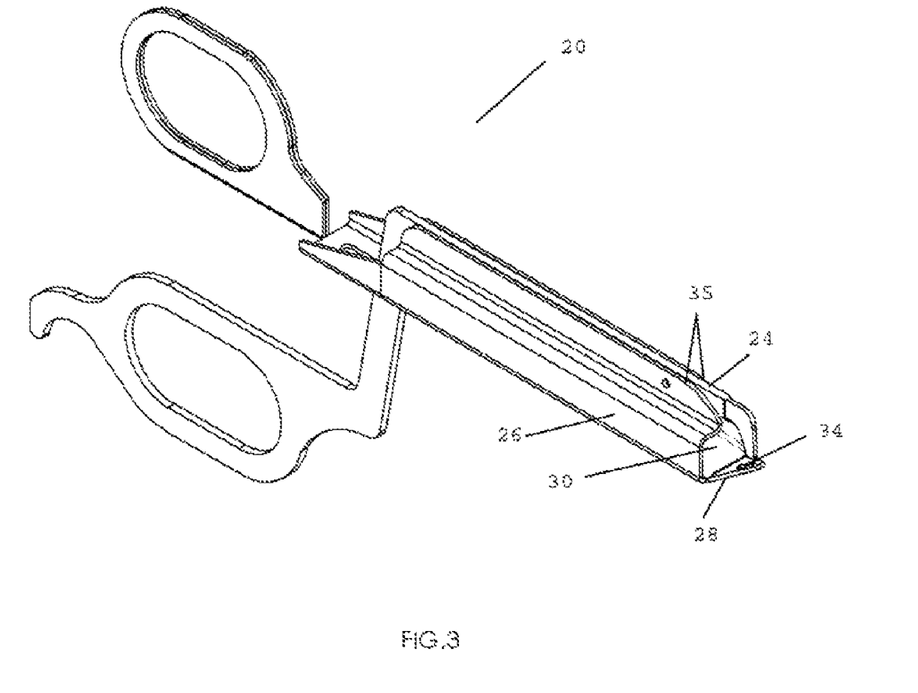
FIG. 3 is a perspective view of the surgical staple remover in an open position, in accordance with one embodiment of the present invention.

FIG. 3 is a perspective view of the surgical staple remover 20 in an open position, in accordance with one embodiment of the present invention. The perspective view of FIG. 3 more clearly shows the triangular shape of the upwards sloped planar element 28 and the cutout 34. FIG. 3 also shows the opening 30 of housing 26 and the gap between the two parallel flanges 35. Also shown is the portion of the second elongated element 24 located within the gap. For clarity, FIG. 3 does not show the spring loaded element 51.

Figure 4:
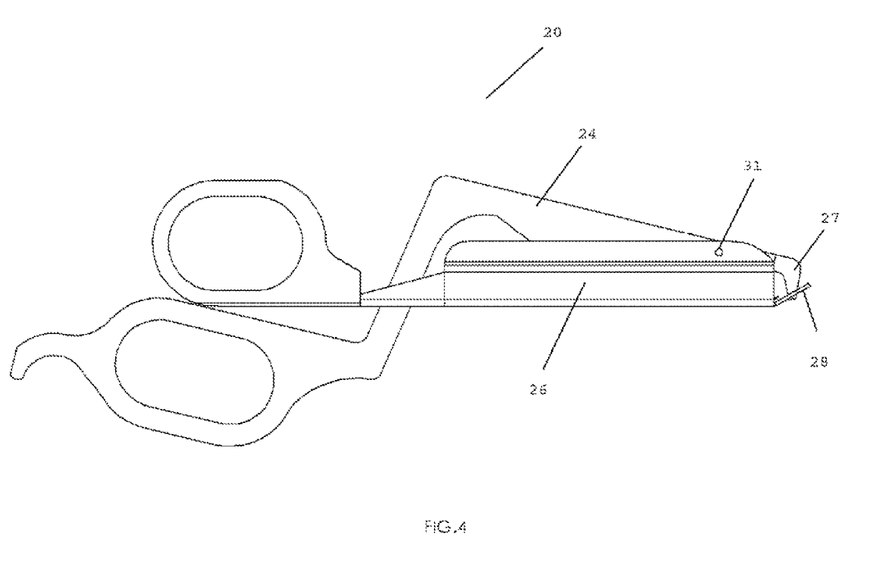
FIG. 4 is a side view of the surgical staple remover in a closed position, in accordance with one embodiment of the present invention.

FIG. 4 is a side view of the surgical staple remover 20 in a closed position, in accordance with one embodiment of the present invention. The side view of FIG. 4 shows the element 24 pivoting about pivot 31 and moving protrusion 27 into the upwards sloped planar element 28 and the cutout 34 (now shown via the side view). The closing of the surgical staple remover 20 results in the deformation and removal of a surgical staple, as described in greater detail below. Note FIG. 4 does not show the spring loaded element 51 since it has retracted into the housing 26, which is a result of the surgical staple remover 20 being in a closed position. The action performed by the spring loaded element 51 is described in greater detail below. Although not shown in FIG. 4, in one embodiment the surgical staple remover 20 may include a miniature battery-powered LED on top of the housing 26, wherein the LED points at the service end of the apparatus 20 so as to illuminate the area surrounding the staple being removed.

Figure 5:
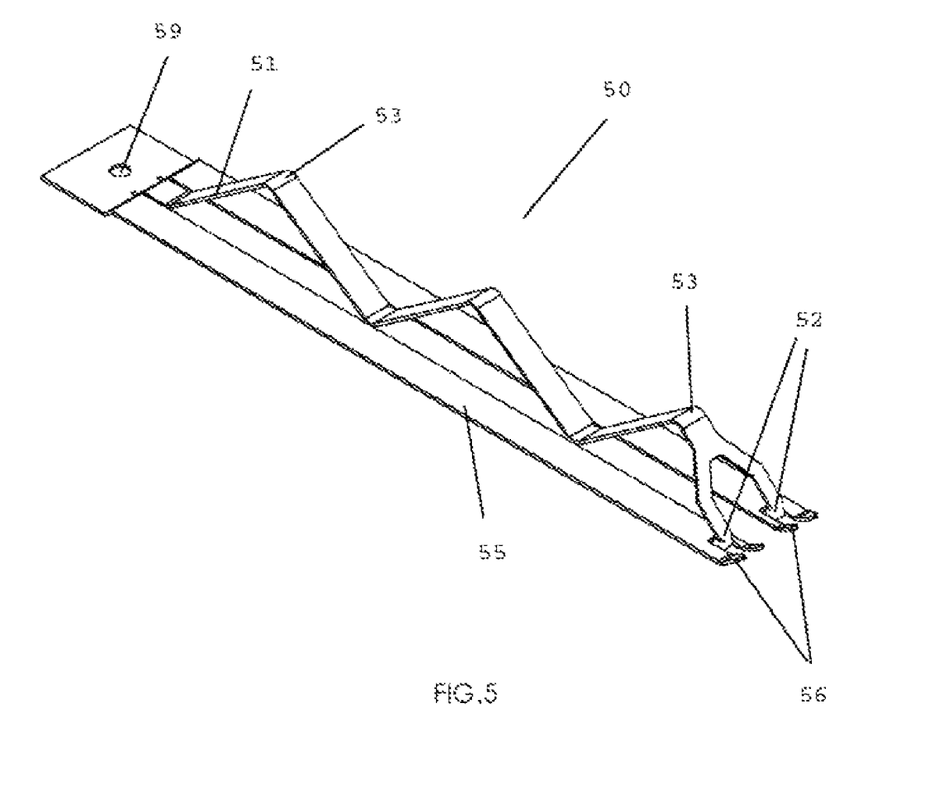
FIG. 5 is a perspective view of the interior element of the surgical staple remover apparatus, in accordance with one embodiment of the present invention.

FIG. 5 is a perspective view of the interior element 50 of the surgical staple remover apparatus 20, in accordance with one embodiment of the present invention. The perspective view of FIG. 5 shows the interior element 50, which is located in the housing 26, comprises a spring loaded element 51 having one or more hooks 52 on a distal end, wherein when the spring loaded element is at rest it retains is native shape and wherein when the spring loaded element is laterally compressed, it extends outwards. When assembled with the apparatus 20, at rest the spring loaded element 51 remains within the housing 26, and wherein when the handles 21, 23 are apart, the spring loaded element 51 is laterally compressed by the bottom side of element 24 and extends out of the housing 26 so as to grip a removed surgical staple 29, and wherein when the handles are thereafter squeezed and brought together, the spring loaded element 51 contracts and moves the removed surgical staple 29 into the housing 26.

The spring loaded element 51 may comprise a strip of a shape memory alloy that includes one or more bends 53, such that lateral compression of the spring loaded element 51 causes it to extend. Also note the hook 52 may comprise a dual pronged hook.

The perspective view of FIG. 5 also shows that the interior element 50 includes strip element 55, which is located on a bottom interior surface of the housing 26, such that when the spring loaded element 51 contracts and moves the removed surgical staple 29 into the housing 26, the removed surgical staple 29 is moved under the strip element 55 and held in place by same. Note the strip element 55 is secured to the bottom interior surface of the housing 26 via a fastener inserted through orifice 59. The spring loaded element 51 may integrally formed with the strip element 55. In one embodiment, the strip element 55 include two separate strips, wherein the ends of each strip 55 includes an upwardly-curved tip 56, so as to facilitate movement of the removed surgical staple 29 under the strip element 55. In another embodiment, each strip element 55 includes a bottom-facing protrusion sub-distally from the upwardly-curved tip 56, so as to inhibit distal movement of a removed staple 29 that has been moved under the strip element 55 past the protrusion. In another embodiment, each upwardly-curved tip 56 of each strip element 55 is split into two parallel elements or fingers such that each hook 52 lies within the gap between the parallel fingers when the element 50 is at rest (see FIG. 1).

Figure 6:
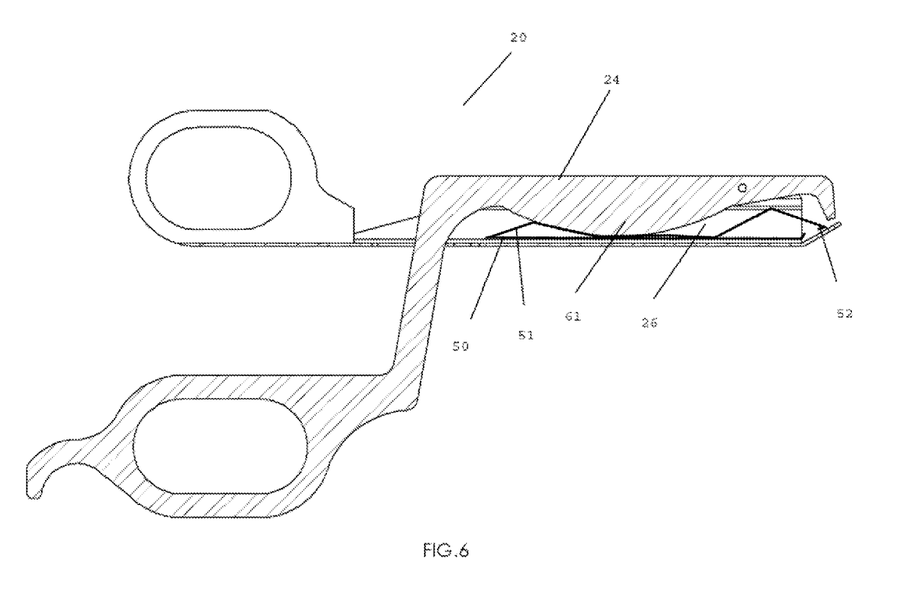
FIG. 6 is a cross-sectional view of the surgical staple remover in an open position, in accordance with one embodiment of the present invention.

The process of utilizing the surgical staple remover apparatus 20 according to one embodiment of the present invention will now be described with reference to FIGS. 6-8. FIG. 6 is a cross-sectional view of the surgical staple remover 20 in an open position, with the interior element 50 being in a compressed state and extending from the housing 26. Note the second elongated element 24 includes a protruding bulge or segment 61 that extends a portion of a length of the second elongated element 24. The spring loaded element 51 of interior element 50 has been laterally compressed by segment 61 of element 24 and extends outside the housing 26 so that the hook 52 extends over the planar element 28. In this position, the spring loaded element 51 possesses potential energy as it is placed under tension and in response the element 51 holds a force to return the spring loaded element 51 to its original shape.

In the open position of FIG. 6, the planar element 28 of surgical staple remover 20 is placed under a surgical staple. In doing so, the hook 52 extends over the surgical staple so as to grasp it or in a position so that hook 52 may grasp the staple as the hook retracts into the housing 26. In the open position of FIG. 6, the hook 52 may extend laterally over and beyond the staple so that the hook 52 grabs or hooks the staple when the hook 52 retracts into the housing 26. Alternatively, in the open position of FIG. 6, the hook 52 extends laterally just over the staple so as to grasp the staple. Regardless, at this point, the hook 52 is ready to pull the staple into the housing 26 when the surgical staple remover 20 moves into a closed position.

Figure 7:
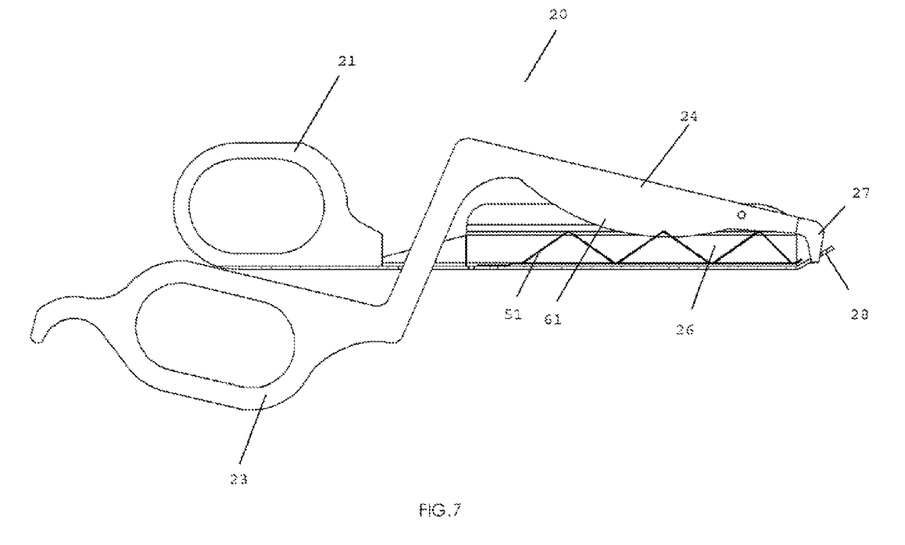
FIG. 7 is a cross-sectional view of the surgical staple remover in a closed position, in accordance with one embodiment of the present invention.

FIG. 7 is a cross-sectional view of the surgical staple remover 20 in a closed position. As the handles 21, 23 are brought together, a surgical staple is deformed due to it compression between protrusion 27 and planar element 28 and therefore the staple is ready for removal. As second elongated element 24 moves upwards, so does the protruding bulge or segment 61 and therefore compression of element 51 is alleviated, which allows element 51 to return to its natural state and retract into housing 26, bringing the removed staple (which hooks 52 has grabbed) with it. Specifically, as the hook 52 drags the staple over the interior bottom surface of the housing 26, it pulls the staple under the strip 55. Note the strip 55 includes an upwardly-curved tip 56, so as to facilitate movement of the removed surgical staple 29 under the strip element 55, and a bottom-facing protrusion sub-distally from the upwardly-curved tip 56, so as to inhibit distal movement of a removed staple 29 that has been moved under the strip element 55 past the protrusion. In this manner, multiple surgical staples can be quickly and easily removed using the apparatus 20 and securely captured inside of the apparatus 20.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

The invention claimed is:

1. A surgical staple remover apparatus, comprising:
a first elongated element having a handle on one end and a downward facing protrusion on the other end;
a second elongated element having a handle on one end and an upwards sloped planar element on the other end, wherein the first and second elongated elements are pivotally connected such that moving the handles into close proximity results in moving the protrusion and planar element into close proximity and such that moving the handles apart results in separating the protrusion and planar element;
a cutout located at a midpoint of a tip of the upwards sloped planar element, such that moving the handles into close proximity results in moving the protrusion into the cutout of the planar element, wherein placing the planar element under a surgical staple and moving the handles into close proximity, results in the protrusion pressing against a crown of the surgical staple, thereby deforming the surgical staple so as to remove it;
a housing running a length of the second elongated element, beginning substantially at the upwards sloped planar element and including an opening facing the planar element; and
a spring loaded element located within the housing and having a hook on a distal end, wherein when the handles are separated, the spring loaded element is laterally compressed and extends out of the housing so as to grip a removed surgical staple, and wherein when the handles are moved into close proximity, the spring loaded element is at rest and contracts into the housing with the removed surgical staple.

2. The surgical staple remover apparatus of claim 1, further comprising:
a strip element located on a bottom interior surface of the housing, such that when the spring loaded element contracts and moves the removed surgical staple into the housing, the removed surgical staple is moved under the strip element and held in place by same.

3. The surgical staple remover apparatus of claim 2, wherein a handle comprises an oval shaped element for accommodating an individual's fingers.

4. The surgical staple remover apparatus of claim 3, wherein the downward facing protrusion comprises a curved element that protrudes downwards from one end of the first elongated element, the tip of which includes a footprint for placement on top of a crown of a surgical staple.

5. The surgical staple remover apparatus of claim 4, wherein the upwards sloped planar element comprises a triangular shaped element having a size and shape that allows its complete insertion underneath a crown of a surgical staple.

6. The surgical staple remover apparatus of claim 5, wherein the cutout located at a midpoint of a tip of the upwards sloped planar element comprises a narrow strip that corresponds to a profile of the protrusion.

7. The surgical staple remover apparatus of claim 6, wherein the first and second elongated elements are pivotally connected at a pivot point that is closer to the handles than the distal ends of the first and second elongated elements.

8. The surgical staple remover apparatus of claim 7, wherein the housing comprises an elongated substantially rectangular box running a length of the second elongated element, beginning at the upwards sloped planar element and including an opening facing the planar element.

9. The surgical staple remover apparatus of claim 8, wherein the housing comprises flange that runs along a top length of the housing, and wherein the pivot point is located in the flange.

10. The surgical staple remover apparatus of claim 9, wherein the flange comprises two parallel flanges that are in close proximity but having a gap between them, and wherein a portion of the second elongated element is located within the gap when the handles are in close proximity.

11. The surgical staple remover apparatus of claim 10, wherein the second elongated element further comprises a protruding segment that extends a portion of a length of the second elongated element, such that the protruding segment of the second elongated element extends through the gap and into the housing when the handles are separated, thereby compressing the spring loaded element laterally, resulting in the spring loaded element extending out of the housing.

12. The surgical staple remover apparatus of claim 2, wherein the spring loaded element comprises a strip of a shape memory alloy that includes one or more bends, such that lateral compression of the spring loaded element causes it to extend.

13. The surgical staple remover apparatus of claim 12, wherein the spring loaded element comprises a dual pronged hook at its distal end.

14. The surgical staple remover apparatus of claim 13, wherein the spring loaded element is integrally formed with the strip element located on the bottom interior surface of the housing.

15. The surgical staple remover apparatus of claim 14, wherein the strip element includes an upwardly-curved tip, so as to facilitate movement of the removed staple under the strip element.

16. The surgical staple remover apparatus of claim 15, wherein the strip element includes a bottom-facing protrusion sub-distally from the upwardly-curved tip, so as to inhibit distal movement of a removed staple that has been moved under the strip element past the protrusion.

17. The surgical staple remover apparatus of claim 2, wherein the apparatus is composed of any one of stainless steel, a metal alloy, plastic, or a plastic derivative.

18. The surgical staple remover apparatus of claim 2, wherein the apparatus is composed of a disposable material.

19. A surgical staple remover apparatus, comprising:
a first elongated element comprising a stamp manufactured planar metallic sheet, the first elongated element having a handle on one end and a downward facing protrusion on the other end;
a second elongated element comprising a stamp manufactured planar metallic sheet, the second elongated element having a handle on one end and an upwards sloped planar element on the other end, wherein the first and second elongated elements are pivotally connected such that moving the handles into close proximity results in moving the protrusion and planar element into close proximity and such that moving the handles apart results in separating the protrusion and planar element;
a cutout located at a midpoint of a tip of the upwards sloped planar element, such that moving the handles into close proximity results in moving the protrusion into the cutout of the planar element, wherein placing the planar element under a surgical staple and moving the handles into close proximity, results in the protrusion pressing against a crown of the surgical staple, thereby deforming the surgical staple so as to remove it;

a housing running a length of the second elongated element, beginning substantially at the upwards sloped planar element and including an opening facing the planar element, wherein the housing comprises:
- an elongated substantially rectangular box running a length of the second elongated element; and
- two parallel flanges that run along a top length of the housing, wherein the two parallel flanges are in close proximity but having a gap between them, and wherein a portion of the second elongated element is located within the gap when the handles are in close proximity; and an interior unit composed of a single strip of shape memory alloy, the interior unit located within the housing, the interior unit comprising:
- a spring loaded element having a dual-pronged hook on a distal end, wherein when the handles are separated, the spring loaded element is laterally compressed and extends out of the housing so as to grip a removed surgical staple, and wherein when the handles are moved into close proximity, the spring loaded element is at rest and contracts into the housing with the removed surgical staple; and
- a strip element located on a bottom interior surface of the housing, such that when the spring loaded element contracts and moves the removed surgical staple into the housing, the removed surgical staple is moved under the strip element and held in place by same.

20. The surgical staple remover apparatus of claim 19, further comprising an LED positioned on top of the housing and arranged so as to illuminate an area proximal to the upwards sloped planar element.

* * * * *